(12) United States Patent
Mueller et al.

(10) Patent No.: US 11,202,606 B2
(45) Date of Patent: Dec. 21, 2021

(54) DETECTION OF ANISOTROPIC BIOLOGICAL TISSUE

(71) Applicant: KONINKLIJKE PHILIPS N.V., Eindhoven (NL)

(72) Inventors: Manfred Mueller, Eindhoven (NL); Bernardus Hendrikus Wilhelmus Hendriks, Eindhoven (NL); Gerhardus Wilhelmus Lucassen, Eindhoven (NL); Torre Michelle Bydlon, Melrose, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1084 days.

(21) Appl. No.: 15/567,178

(22) PCT Filed: Apr. 12, 2016

(86) PCT No.: PCT/EP2016/057948
§ 371 (c)(1),
(2) Date: Oct. 17, 2017

(87) PCT Pub. No.: WO2016/166067
PCT Pub. Date: Oct. 20, 2016

(65) Prior Publication Data
US 2018/0098730 A1    Apr. 12, 2018

(30) Foreign Application Priority Data

Apr. 17, 2015    (EP) .................................... 15164075

(51) Int. Cl.
*A61B 5/00*    (2006.01)
(52) U.S. Cl.
CPC .......... *A61B 5/4893* (2013.01); *A61B 5/0075* (2013.01); *A61B 5/0082* (2013.01)

(58) Field of Classification Search
None
See application file for complete search history.

(56) References Cited

U.S. PATENT DOCUMENTS

| | | |
|---|---|---|
| 5,284,154 A | 2/1994 | Raymond |
| 5,987,346 A | 11/1999 | Benaron |
| | (Continued) | |

FOREIGN PATENT DOCUMENTS

| | | |
|---|---|---|
| WO | 199902956 A2 | 1/1999 |
| WO | 0015101 A1 | 3/2000 |
| | (Continued) | |

OTHER PUBLICATIONS

Müller, M. "Nerve Detection in Optical Spectra from Ex-Vivo Pig Legs", Technical Note PR-TN 2014/00045, 2014.

(Continued)

*Primary Examiner* — Pascal M Bui Pho
*Assistant Examiner* — Marjan Saboktakin (57) ABSTRACT

A system for detection of optically anisotropic tissue is provided. The system comprises an optical source, an optical detector, a processing unit and a probe. The probe has a shaft with a longitudinal axis and a front end, and a plurality of optical fibers; wherein an end of each of the optical fibers is arranged at the front end of the shaft, and at least one of the optical fibers is a source optical fiber adapted to transmit optical radiation emitted from the optical source to a tissue adjacent to the front end of the shaft. Another one of the optical fibers is a detector optical fiber adapted to transmit optical radiation reflected from the tissue to the optical detector, so that an optical path through the tissue is defined, wherein the optical paths differ from each other with respect to their spatial orientation, and wherein the optical paths cross each other. The processor is configured to control the optical source to emit optical radiation, to receive a signal generated by the optical detector based on the optical (Continued)

radiation reflected by the tissue, to determine a plurality of optical spectra of the reflected optical radiation based on the received signal, wherein the optical spectra are obtained of the same location from at least two different directions, wherein the measurement of the optical spectra is performed either simultaneously or sequentially, and to compare the plurality of optical spectra, wherein the optical spectra relate to optical radiation of the different optical paths thus allowing the detection of anisotropic tissue using differences between the optical spectra.

20 Claims, 5 Drawing Sheets

(56) References Cited

U.S. PATENT DOCUMENTS

| | | | |
|---|---|---|---|
| 6,697,657 B1 * | 2/2004 | Shehada | A61B 5/0075 |
| | | | 600/317 |
| 7,289,211 B1 | 10/2007 | Walsh | |
| 8,239,139 B2 | 8/2012 | Mycek | |
| 8,954,133 B1 | 2/2015 | Hanlon | |
| 2003/0135122 A1 | 7/2003 | Bambot | |
| 2004/0021848 A1 * | 2/2004 | Bambot | G01N 21/6486 |
| | | | 356/39 |
| 2008/0009751 A1 * | 1/2008 | Berndt | A61B 1/07 |
| | | | 600/478 |
| 2009/0270702 A1 * | 10/2009 | Zeng | A61B 5/1459 |
| | | | 600/323 |
| 2011/0206291 A1 | 8/2011 | Kashani et al. | |
| 2013/0218027 A1 | 8/2013 | Nagale | |
| 2014/0117256 A1 | 5/2014 | Mueller | |
| 2017/0224220 A1 * | 8/2017 | Tunnell | G01J 3/02 |

FOREIGN PATENT DOCUMENTS

| | | |
|---|---|---|
| WO | 2007100648 A2 | 9/2007 |
| WO | 2007121009 A2 | 10/2007 |
| WO | 2011049758 A1 | 4/2011 |
| WO | 2012123869 A2 | 9/2012 |
| WO | 2014026200 A1 | 2/2014 |

OTHER PUBLICATIONS

Shuaib, Ali, "Characterizing Optical Properties in Fibrous Tissues", Dissertation, Dec. 2011.

Schols, Rutger M. et al "Differentiation Between Nerve and Adipose Tissue Using Wide-Band (350-1,830nm) in vivo Diffuse Reflectance Spectroscopy", Lasers in Surgery and Medicine, 2014.

Hendriks, B.H.W. et al "NerveSpect Study NKI: In Vivo Human Nerve Detection with Diffuse Optical Spectroscopy", Technical Note PR-TN 2013/00635, 2013.

* cited by examiner

FIG. 8

DETECTION OF ANISOTROPIC BIOLOGICAL TISSUE

CROSS-REFERENCE TO PRIOR APPLICATIONS

This application is the U.S. National Phase application under 35 U.S.C. § 371 of International Application No. PCT/EP2016/057948, filed on Apr. 12, 2016, which claims the benefit of European Patent Application No. 15164075.2, filed on Apr. 17, 2015. These applications are hereby incorporated by reference herein.

FIELD OF THE INVENTION

The invention generally relates to a system for detection of optically anisotropic biological tissue in optical spectroscopy. The invention further relates to a computer program allowing steps of a process resulting in a detection of optically anisotropic biological tissue to be performed automatically.

BACKGROUND OF THE INVENTION

In various clinical interventions, it is important that nerves can be localized accurately. For example, detecting nerves may preserve nerves or prevent resection during surgical procedures and allows for localized injection of pain relieving medicaments nearby nerves. Currently localization procedures consist of localizing nerves in imaging modalities such as ultrasound or magnetic resonant imaging (MRI), whereby it may be sometimes difficult to find and identify tissue as being nerves.

There is a clinical desire for confirmation of the presence of the nerve in order to prevent complications. The gold standard for confirmation of this presence is stimulation of the nerves by using electrical stimulation.

U.S. Pat. No. 5,284,154 describes a method and apparatus for locating and identifying the function of specific peripheral nerves. The apparatus of U.S. Pat. No. 5,284,154 includes a stimulus delivery means and a response-detecting means. Electrical stimulation is used for example to locate, identify the function of, and guard against the inadvertent cutting of specific nerves during surgical procedures.

Electrical stimulation has several disadvantages, for example it may induce electrical burns in patients, which if unseen by surgeons can result in perforated organs and can also lead to peritonitis. Electrical stimulation also has a low sensitivity. Recently, stimulation of nerves using optical energy has received increased attention in the literature. A practical device for in-vivo application is suggested in WO 2012/123869 which relates to the identification and stimulation of nerve tissues, and more in particular to a method, apparatus and probe for optical nerve localization and optical nerve stimulation. It is suggested to combine in a single apparatus the localization and the verification of the presence of nerve tissue by optical stimulation. The stimulation is detected by monitoring the variations based on thermal sensitive spectroscopic features of light scattering from the area of the stimulated nervous tissue.

SUMMARY OF THE INVENTION

It may be seen as an object of the invention to improve the discrimination of nerve tissue (and other anisotropic tissues like tendons) from other biological tissue types. This and other objects are solved by the system and the computer program according to the independent claims, respectively. Further embodiments are described in the dependent claims.

In general, a tissue classification system is suggested which is configured to discriminate/detect an optical anisotropic tissue (like nerve) using diffuse reflectance spectroscopy (DRS) that measures the DRS spectrum under two or more different directions (either simultaneously or sequentially) at the same location. The detection algorithm then uses the differences between these different spectra to discriminate/detect the desired tissue.

The measurement under different directions/angles can be facilitated by the hardware (e.g. by using multiple source and/or detection optical fibers under significantly different angles and not averaging).

The detection algorithm will typically start by determining whether the tissue at the current location is isotropic or not. If the tissue is isotropic, then it is not nerve, tendon, etc. If the tissue is anisotropic then the algorithm will determine from the spectra whether it is the desired or another anisotropic tissue.

According to an embodiment, a system for detection of optically anisotropic tissue may comprise an optical source, an optical detector, a probe and a processing unit. Either the optical source or the optical detector may be wavelength-selective. The probe may have a shaft with a longitudinal axis and a front end, and a plurality of optical fibers, wherein an end of each of the optical fibers is arranged at the front end of the shaft. At least one of the optical fibers may be a source optical fiber adapted to transmit optical radiation emitted from the optical source to a tissue adjacent to the front end of the shaft and another one of the optical fibers may be a detector optical fiber adapted to transmit optical radiation reflected from the tissue to the optical detector, so that an optical path through the tissue is defined. The processing unit may be configured (i) to control the optical source to emit optical radiation, (ii) to receive a signal generated by the optical detector based on the optical radiation reflected by the tissue, (iii) to determine an optical spectrum of the reflected optical radiation, based on the received signal, and (iv) to compare at least two spectra, wherein the spectra relate to optical radiation with different optical paths, wherein the optical paths differ from each other with respect to their spatial orientation.

It is noted that an optical spectrum may encompass one or more discrete wavelengths or wavelength regions, that the optical source may be a broadband optical source, i.e. including wavelengths within the visible to infrared spectral region, or a visible white light source and that the detector optical fiber may be connected to a spectrometer.

In the following, geometrical aspects will be defined for a better understanding. First of all, the probe may include a longitudinal main axis, usually the center axis of a rotationally symmetrical shaft. If the probe is a needle or another intrusive probe the longitudinal main axis will be along the direction of movement inside the biological tissue. Further, the tip portion of the probe may be cut at an angle to the main axis. The angle may be substantially perpendicular to the main axis (forming a blunt probe end) but may also be inclined to the main axis (forming a bevel). The pointed tip of a bevel may be considered as being directed to the 'front' of the needle and may form an acute angle with the shaft. Looking from the 'side', i.e. 'laterally', it is possible to recognize the angle between the bevel and the main axis.

It should be noted that the end surface of an optical fiber at an opening in the front surface may have a circular shape or a more or less oval shape in case of a substantially circular cross section of the fiber in an inclined front surface.

Depending on the angle at which the optical fiber ends at the bevel surface, the shape of the end surface of the optical fiber will be affected and therefore also the direction of the emitted or received optical radiation. For a needle the optical path may be substantially in the direction of movement of the needle through the tissue, enabling the needle to 'look ahead'.

A pair of optical fiber ends may define an optical path, with optical radiation emitted from a first optical fiber, reflected in tissue and received in a second optical fiber of the pair. Depending on the position of the respective optical fiber ends, the optical path will have a spatial orientation relative to the shaft of the probe. Consequently, each pair of optical fibers will define an optical path, wherein the spatial orientation will differ as soon as different optical fibers form a pair or as soon as the probe is rotated. The optical path may be ahead in the direction where nerve detection may be intended.

According to an embodiment, the probe may comprise one detector optical fiber and at least two source optical fibers, wherein a first optical path is defined from a first source optical fiber to the detector optical fiber and a second optical path is defined from a second source optical fiber to the detector optical fiber. In this embodiment, the optical path from the first source optical fiber to the detector optical fiber is oriented transversely to the optical path from the second source optical fiber to the detector optical fiber.

According to another embodiment, the probe may comprise at least two detector optical fibers and at least two source optical fibers, wherein a first optical path is defined from a first source optical fiber to a first detector optical fiber and a second optical path is defined from a second source optical fiber to a second detector optical fiber. In this embodiment, the optical path from the first source optical fiber to the first detector optical fiber is oriented transversely to the optical path from the second source optical fiber to the second detector optical fiber.

The first optical path may be oriented relative to the second optical path with an angle of at least 60 degrees. According to an embodiment, the angle between the first and second optical paths may be at least 70 degrees.

Furthermore, it is advantageous if the two optical paths cross each other.

According to another embodiment, the system comprises two optical sources. In addition or alternatively, the system may further comprise an optical switch or modulator, to distribute the optical radiation of one optical source to different optical fibers.

As described in more detail below, the invention is based on the idea that a biological tissue is measured with differently oriented optical paths. This may also be achieved with a probe including one pair of optical fibers, wherein the probe is rotated between two measurements. Consequently, the system may further comprise a means for actively and/or automatically rotating the probe about its longitudinal axis. It is noted that a rotation of the probe may also be of advantage, with two optical paths being provided by the probe.

According to another embodiment, the system may further comprise a means for polarizing the optical radiation emitted from the optical source. The means for polarizing may be capable of changing the polarization direction, i.e. may be capable of polarizing the optical radiation with different polarization directions. With such an embodiment, two different (for example orthogonal) polarization measurements may be employed. When the tissue is anisotropic, the two measurements will be different. A detection algorithm is employed to detect the difference between the spectra measured for the different polarization directions and uses this information to discriminate/detect the desired tissue.

According to an embodiment, the probe may further comprise a channel for injecting or extracting a fluid. For example, an injection of a narcotic fluid may be possible in a direct vicinity of a nerve, as soon as the nerve has been detected by means of the probe, with the effect that a smaller amount of the narcotic fluid may have the intended anaesthetic effect on the nerve.

According to an embodiment, the system may further comprise a console including the optical source, the optical detector and the processing unit for processing the signals provided by the optical detector, the console being adapted for in-vivo tissue inspection. The optical source or the optical detector may provide wavelength selectivity. The optical source may be one of a laser, a light-emitting diode or a filtered optical source or a broad-band optical source, and the console may further comprise one of an optical fiber switch, a beam splitter or a dichroic beam combiner. Furthermore, the device may be adapted to perform at least one out of the group consisting of diffuse reflectance spectroscopy, diffuse optical tomography, differential path length spectroscopy, fluorescence spectroscopy, and Raman spectroscopy. The console may comprise at least one spectrometer.

According to an embodiment, the probe may further comprise a coil for electromagnetic tracking. For example, the tip of the probe may be equipped with such a small coil. This offers the capability of controlled navigation of the probe and, at the same time, it also offers an on-the-spot tissue confirmation using spectral sensing as described herein.

According to an embodiment, the probe may further comprise a radiopaque material at the distal end portion of the shaft for enhancing the visibility of that portion in a fluoroscopic image. Furthermore, the distal end portion of the shaft of the probe may be configured for cauterization. This would prevent the risk of excessive bleeding at the insertion site.

According to another aspect, a method for detecting optically anisotropic tissue in a portion of tissue. The method comprises the steps of:
A1) controlling a light source to emit light having two different optical paths, wherein the optical paths cross each other;
A2) receiving a signal which has been generated by an optical detector based on light reflected by the portion of tissue;
A3) determining a plurality of optical spectra (Sp1, Sp2) of the reflected light based on the received signal, wherein the optical spectra are obtained from at least two different directions at the same location, wherein the measurement is performed either simultaneously or sequentially;
A4) comparing the plurality of optical spectra (Sp1, Sp2), wherein the optical spectra relate to optical radiation of the different optical paths (Lp1, Lp2).

According to another aspect, a computer program is suggested to be executed on a processing unit of a system as described above so as to automatically perform steps of a method for detection of optically anisotropic biological tissue. The computer program may comprise instructions for (i) controlling the optical source to emit optical radiation, (ii) receiving a signal generated by the optical detector based on the optical radiation reflected by the tissue, (iii) determining an optical spectrum of the reflected optical radiation, based on the received signal, and (iv) comparing at least two spectra, wherein the spectra relate to optical radiation with different optical paths, wherein the optical paths differ from each other with respect to their spatial orientation.

According to an embodiment, the computer program may further comprise instructions for controlling a rotational orientation of the probe. For example, the system may comprise a means for driving a rotation of the probe mechanically, pneumatically, hydraulically or otherwise. Those means may be controlled by the processing unit when executing corresponding instructions of a computer program.

In addition or alternatively, the computer program may comprise instructions for controlling a polarization direction of the emitted optical radiation.

The aspects defined above and further aspects, features and advantages of the present invention may also be derived from the examples of embodiments to be described hereinafter and are explained with reference to examples of embodiments. The invention will be described in more detail hereinafter with reference to examples of embodiments but to which the invention is not limited.

BRIEF DESCRIPTION OF THE DRAWINGS

The illustration in the drawings is schematically only and not to scale. It is noted that similar elements are provided with the same reference signs in different Figures, if appropriate.

DETAILED DESCRIPTION OF EMBODIMENTS

Spectra from a given tissue type tend to look similar. The respective tissue "fingerprint" (characteristic spectrum) is used to discriminate between tissue types. Typically, the fingerprint is first extracted/enhanced (for example by fitting the concentration of characteristic chromophores or by calculating principal components) and then these derived features are used to discriminate tissues based on typical machine learning methods such as SVM, CART, cut-off values, or k-nearest-neighbors. For example, it is clear that fat spectra have a different characteristic shape (or fingerprint) than the muscle tissue. For example the fat dip at 1200 nm is nearly always deeper for subcutaneous fat tissue than for muscle tissue.

On the one hand, biological tissues may be optically isotropic, wherein optical isotropy means in this context that the DRS spectrum does not depend on the direction in which the spectrum has been measured. If one source optical fiber and one detector optical fiber is used, the direction in which the spectrum may be measured is the direction from the exit facet of the source optical fiber to the entrance facet of the detector optical fiber. Most biological tissues like fatty tissue and connective tissue are inherently isotropic (that is the cells have no preferred direction or orientation) and are therefore optically isotropic. Even biological tissues whose cells have a preferred direction, like muscle, are often still optically isotropic.

Figure 1:
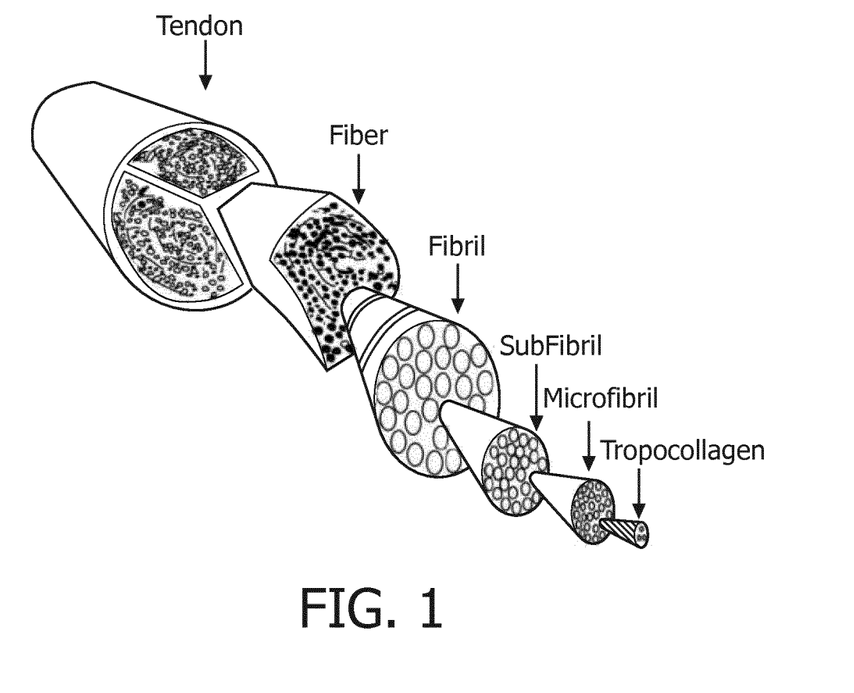
FIG. 1 shows a hierarchical structure of tendon.

On the other hand, some biological tissues are anisotropic. This includes nerves but also tendons and ligaments. That is because tendons/ligaments and nerves are ordered bundles of fibers as shown in FIG. 1. A tendon/ligament consists primarily of collagen. The structure of nerves is similar, with a strong principal axis. As a consequence, the spectrum of nerve or tendon tissue depends strongly on the direction (from the nerve or tendon axis) at which it is measured. There is no longer a single tissue type fingerprint/characteristic spectrum.

Figure 2:
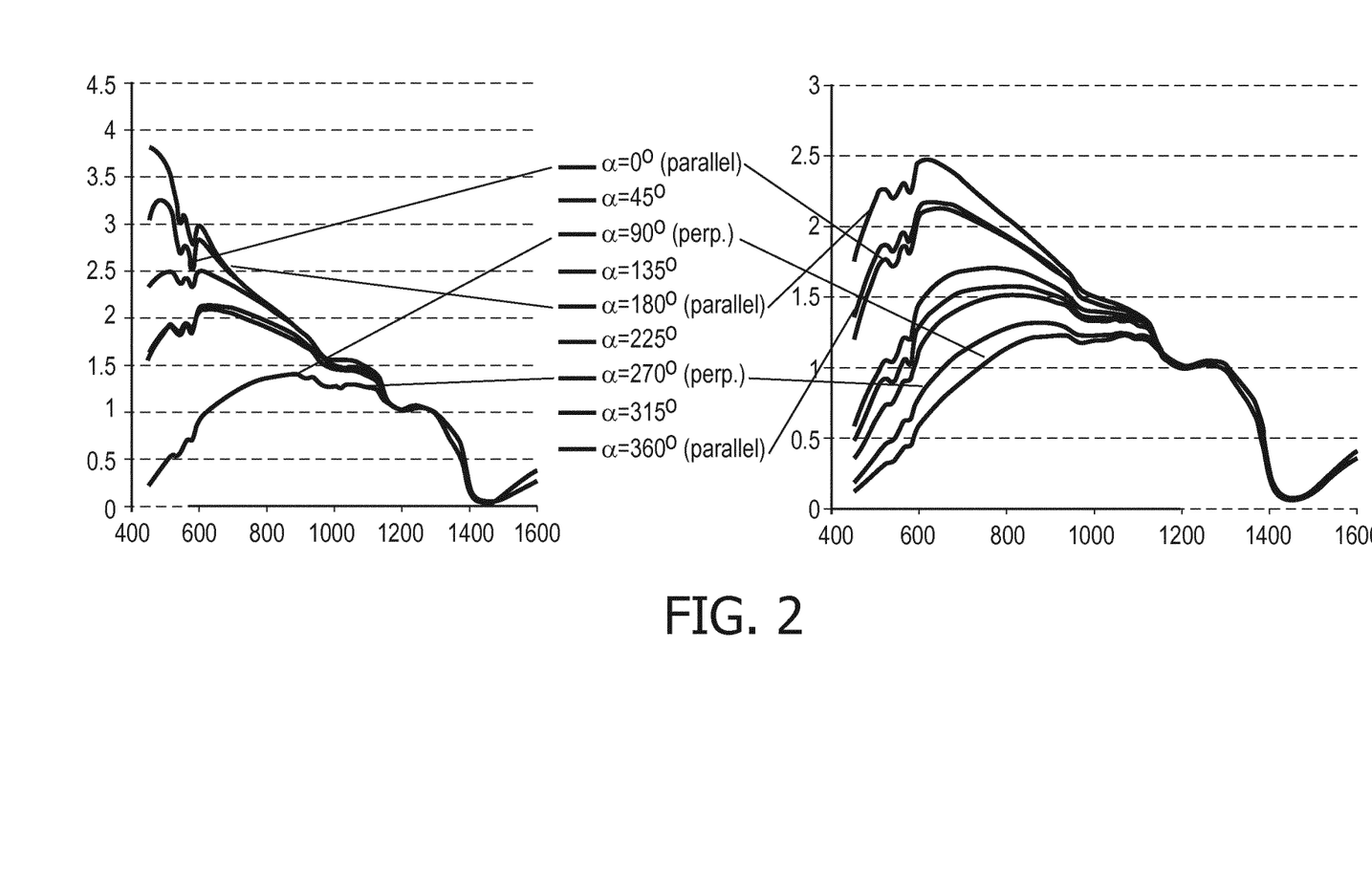
FIG. 2 shows DRS spectra of a nerve in dependence of the angle between the optical path at the probe and the nerve axis.

FIG. 2 illustrates DRS spectra of the same pig nerve (same location) in dependence of the angle between the source/detector optical fiber pair, i.e. the optical path of the probe and the nerve axis. The right graph was measured with the probe perpendicular to the nerve and the probe being rotated around its axis. An angle of 0° or 180° means the direction of the optical path at which the spectrum was measured is parallel to the nerve fibers, at 90° and 270° it is perpendicular. The left spectrum was measured with the probe angled 60° from the perpendicular direction and being rotated around the perpendicular direction.

A DRS system as described herein typically consists of three main components, namely a probe (e.g. a needle) with at least one source optical fiber and one detector optical fiber, a console with at least one optical source and at least one spectrometer including an optical detector, and a processing unit on which a discrimination software may run that makes a tissue classification depending on the optical spectra.

In the following description it is assumed that the system is supposed to detect nerves. The same principle applies for detecting any other anisotropic type of tissue.

Figure 3:
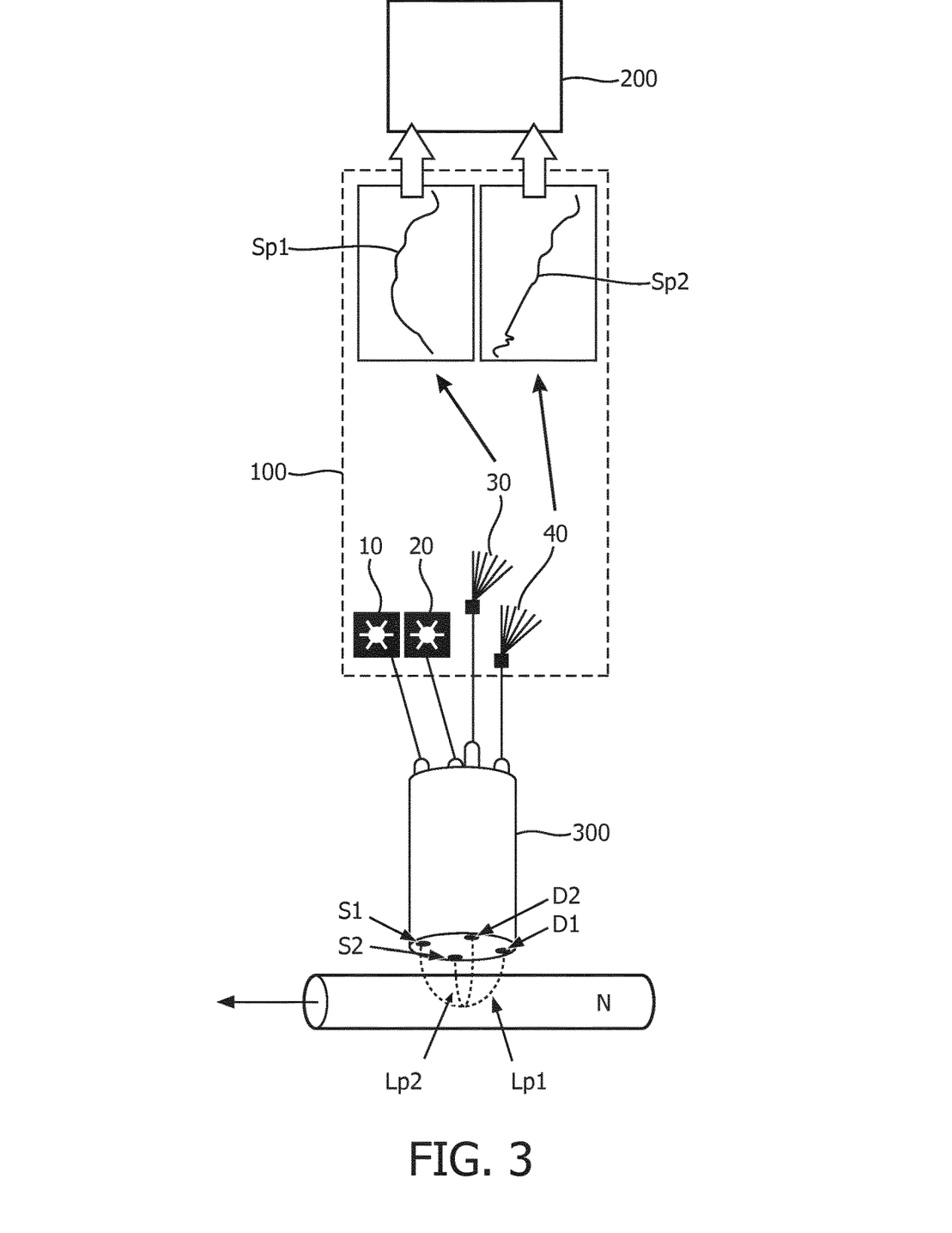
FIG. 3 shows a system including a probe, a console and a processing unit.

In a first embodiment, as shown in FIG. 3, a special fiber optic probe 300 is used that can measure spectra under at least two different directions without the need to rotate the probe. Two source (S1, S2) and two detector (D1, D2) optical fibers together with two optical sources 10, 20 and two spectrometers 30, 40 are used to measure the DRS spectrum at two perpendicular directions Lp1, Lp2. The data processing unit 200 has the (at least) two spectra Sp1, Sp2 as input and a tissue classification (e.g. Nerve or NonNerve) as an output. By using at least two spectra it is easy to distinguish isotropic from non-isotropic tissues. Also it is easier to distinguish different types of non-isotropic tissues. Various ways may be implemented to do the actual processing and classification. For example, the two spectra may be subtracted from each other and the difference spectrum may be used as an input for a classification method like PLSDA, SVM or adaboost.

As shown in FIG. 3, the optical fibers of the probe are connected to an optical console 100. The optical fibers can be understood as optical guides or optical waveguides. The console 100 may comprise at least one optical source 10, 20 in the form of a halogen broadband optical source with a shutter, and at least one optical detector 30, 40. The optical detector providing the functionality of a spectrometer can resolve optical radiation with a wavelength substantially in the visible and infrared regions of the wavelength spectrum, such as from 400 nm to 1700 nm. The combination of optical source and optical detector allows for diffuse reflectance measurements.

Optionally it is also possible that the console is coupled to an imaging modality capable of imaging the interior of the body, for instance when a biopsy is taken under image guidance. On the other hand, also other optical methods can be envisioned like diffuse optical tomography by employing a plurality of optical fibers, differential path length spectroscopy, fluorescence and Raman spectroscopy to extract tissue properties.

A processor transforms the measured spectrum into physiological parameters that are indicative for the tissue state and a monitor may be used to visualize the results. A computer program executable on the processor unit 200 may be provided on a suitable medium such as an optical storage medium or a solid-state medium supplied together with or as part of the processor, but may also be distributed in other forms, such as via the Internet or other wired or wireless telecommunication systems.

For fluorescence measurements the console must be capable of providing excitation optical radiation to at least one source optical fiber while detecting tissue-generated fluorescence through one or more detection optical fibers. The excitation optical source may be a laser (e.g. a semiconductor laser), a light-emitting diode (LED) or a filtered optical source, such as a filtered mercury lamp. In general, the wavelengths emitted by the excitation optical source are shorter than the range of wavelengths of the fluorescence that is to be detected. It is preferable to filter out the excitation optical radiation using a detection filter in order to avoid possible overload of the detector by the excitation optical radiation. A wavelength-selective detector, e.g. a spectrometer, is required when multiple fluorescent entities are present that need to be distinguished from each other.

In case fluorescence measurements are to be combined with diffuse reflectance measurements, the excitation optical radiation for measuring fluorescence may be provided to the same source optical fiber as the optical radiation for diffuse reflectance. This may be accomplished by, e.g., using an optical fiber switch, or a beam splitter or dichroic beam combiner with focusing optics. Alternatively, separate optical fibers may be used for providing fluorescence excitation optical radiation and optical radiation for diffuse reflectance measurements.

Figure 4:
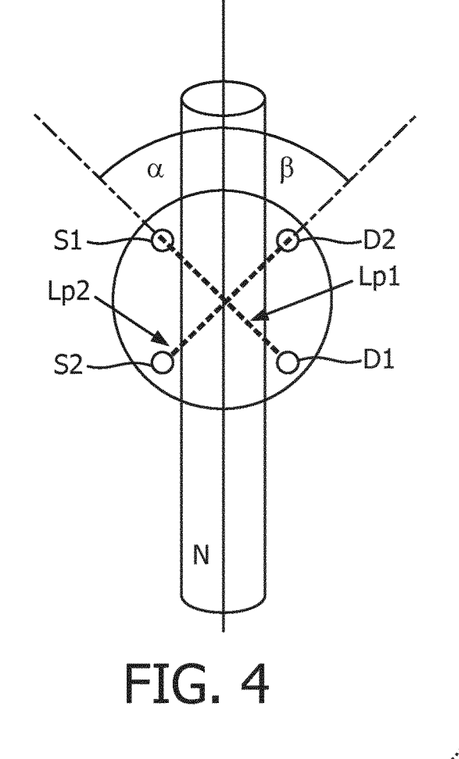
FIG. 4 is a view of the front surface of a probe of FIG. 3.

FIG. 4 is a detailed view of the front surface of the probe of FIG. 3. It is possible to distinguish non-isotropic tissues from isotropic tissues, for most orientations of the probe. However, when the (projected) angle between measurement direction along optical path Lp1 and the nerve axis, α, is (nearly) equal to the (projected) angle between measurement direction along optical path Lp2 and the nerve axis, β, both spectra may be the same. In such a case, a non-isotropic tissue may appear isotropic. This issue can be resolved in various ways. Firstly, instructions for use may be provided for a physician who will typically know the general direction of the nerve he/she is looking for. The incidence of a α≈β situation can be reduced by marking the direction of one measurement on the probe and instructing the user to rotate the probe in such a way that the marked direction aligns with the expected direction of the nerve. Secondly, at least three directions may be measured, as an α≈β situation can only occur if exactly two directions are measured. Thirdly, source and detector optical fibers may be cross-switched.

In the situation in FIG. 4, if one measures one spectrum Sp1 between source optical fiber S1 and detector optical fiber D2 and spectrum Sp2 between detector optical fiber D1 and detector optical fiber D2 one gets again maximum contrast between the spectra. For this to work, one of the optical fibers in the probe has to be connected in such a way that it can be used as either a source or a detector optical fiber.

Figure 5:
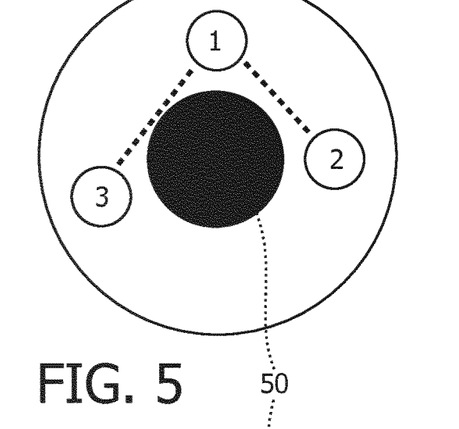
FIG. 5 is a view of the front surface of a probe according to another embodiment.

FIG. 5 shows a variation with two source optical fibers and a common detector optical fiber. For example, the two source optical fibers may be the optical fibers denoted with 2 and 3 and the detector optical fiber may be the optical fiber denoted with 1 in FIG. 5. It will be understood that the same output can be achieved with just a single spectrometer and/or a single optical source, for example by using optical switches or modulators. In any case, it is intended to measure at least two spectra at different angles, for example at approximately right angle. A common detector optical fiber can measure the optical DRS spectrum under two different directions. Using a common detector optical fiber allows the use of a single optical detector and spectrometer.

Figure 6:
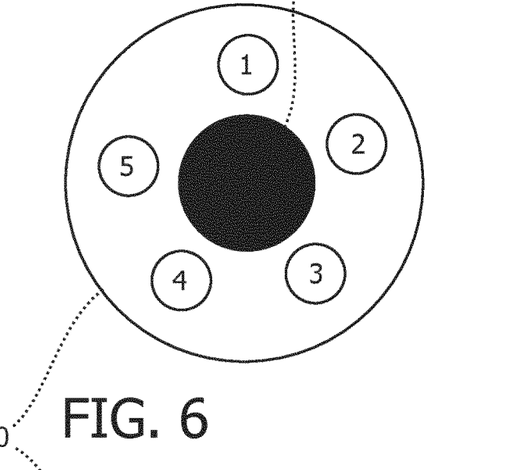
FIG. 6 is a view of the front surface of a probe according to yet another embodiment.
Figure 7:
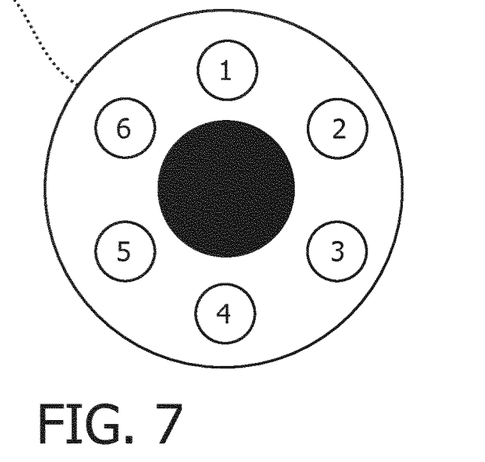
FIG. 7 is a view of the front surface of a probe according to a further embodiment.

It is noted that the area denoted with the reference sign 50 in FIGS. 5 and 6, and consequently also in FIG. 7, may either be a channel for injection or resection of a fluid through the probe or be a further optical fiber which may serve as a source or a detector optical fiber.

FIGS. 6 and 7 show alternative embodiments of probes having at least one detector optical fiber and up to 5 or 6 source optical fibers.

For example, the embodiments of FIGS. 6 and 7 may show a probe with multiple source optical fibers (1, 2, 3, 4, 5 and 6) arranged around a single detector optical fiber 50. These embodiments measure DRS spectra under different angles sequentially by sequentially illuminating individual optical fibers and taking a spectrum. If source optical fibers are arranged on opposite sides of the detector optical fiber, these sources optical fibers can be illuminated at the same time. Ideally subsequent spectra are taken nearly at right angles, to maximize contrast between subsequent spectra. The probe as shown in FIG. 6 could work by illuminating optical fiber 1, then optical fiber 3, then optical fiber 5, then optical fiber 2, then optical fiber 4, then optical fiber 1 again. If one spectrum is measured per illumination, then subsequent spectra are measured at 72 degree angles. Possible switching patterns may be for the embodiment of FIG. 7, first illuminating optical fibers 1 and 4, then optical fibers 2 and 5, then optical fibers 3 and 6, then optical fibers 1 and 4 again. If one spectrum is measured per illumination, then subsequent spectra are measured at 60 degree angles. The switching should be fast enough so that the classification algorithm can make use of at least 3 subsequent spectra to avoid the α≈β problem.

Figure 8:
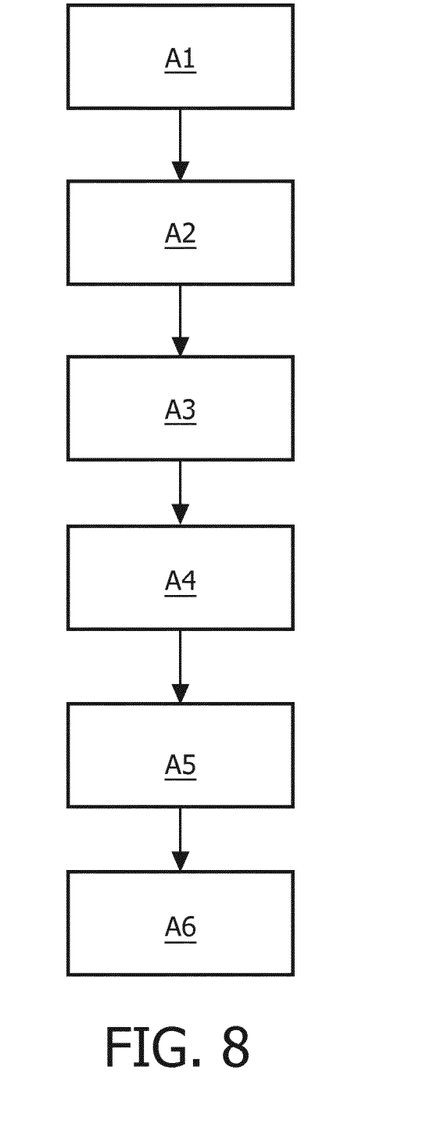
FIG. 8 is a flow chart illustrating steps of a method executable by a computer program.

With reference to FIG. 8, a software solution is described. The flowchart in FIG. 8 illustrates the principles of anisotropic tissue detection. It will be understood that the steps described with respect to the automatically performed method are major steps, wherein these major steps might be differentiated or divided into several sub steps. Furthermore, there might also be sub steps between these major steps. A sub step is only mentioned if that step is important for the understanding of the principles of the method according to the invention.

A demand for an anisotropic detection can be initiated by a user or by the system. The user can initiate an anisotropic detection, when the probe tip is at a location where the user needs to classify the type of tissue with a high degree of certainty. This could for example be just before an injection. The user may initiate an anisotropic detection for example by pressing a button. Otherwise, the system can automatically initiate an anisotropic detection, when the standard classification suspects a nerve, but when the uncertainty is still too high.

According to another aspect of the invention, there is provided a method for detecting optically anisotropic tissue in a portion of tissue, comprising the steps of:

A1) controlling a light source to emit light having two different optical paths, wherein the optical paths cross each other;

A2) receiving a signal which has been generated by an optical detector based on light reflected by the portion of tissue;

A3) determining a plurality of optical spectra (Sp1, Sp2) of the reflected light based on the received signal, wherein the optical spectra are obtained from at least two different directions at the same location, wherein the measurement is performed either simultaneously or sequentially;

A4) comparing the plurality of optical spectra (Sp1, Sp2), wherein the optical spectra relate to optical radiation of the different optical paths (Lp1, Lp2), thus allowing the detection of anisotropic tissue using the differences between the optical spectra.

When performing an anisotropic detection, the at least one optical source is controlled so as to emit optical radiation, in step A1.

In step A2, a signal is received which has been generated by the optical detector based on the optical radiation reflected by tissue.

Based on the received signal, an optical spectrum of the reflected optical radiation is determined in step A3.

At least two of the determined spectra are compared in step A4.

Based on the comparison of the spectra, the system may alert the user to the need to rotate the probe e.g. by a sound signal.

In step A5, if necessary, the probe may be rotated. For example, the probe may be rotated with a rotation by 90° around the axis of the probe, wherein a rotation by 180° or more may be preferred because then the contrast between the spectra is maximized. The rotation may be done slowly so that spectra at different angles are taken more reliably. A marking on the probe can help a user in following the rotation angle. When the probe is not being rotated, the system may utilize different optical paths which are possible with at least three optical fibers.

If the probe is rotated manually the classification unit will acquire a number of spectra measured under different angles, but it will not be obvious which spectra was acquired at which angle. This is not necessary, however. The classification unit can simply pick the two spectra which exhibit the biggest differences. In general these two spectra will have been measured roughly at perpendicular directions.

Additionally, polarization of the emitted optical radiation may be employed in step A6. By employing polarization the anisotropy in the medium, i.e. the inspected tissue can be detected from the difference in signal when optical radiation with different polarization is sent into the optical fiber. Preferably polarization maintaining fibers are used. It is also possible to use normal multimode fibers. In this case the polarization is not fully maintained and only the difference between the two states can be measured and are indicative for an isotropic medium in front of the needle. Furthermore, the optical console contains an optical source and a switch between two states with two different polarizers. A controller may be used to switch the polarization state from state one to the second state and two different measurements may be made. An algorithm then determines whether the medium in front is isotropic. If so the tissue classification algorithm then makes use of this input.

In general, the process is based on the steps A1 to A4. The steps A5 and A6 may be performed additionally or alternatively, if necessary.

While the invention has been illustrated and described in detail in the drawings and foregoing description, such illustration and description are to be considered illustrative or exemplary and not restrictive; the invention is not limited to the disclosed embodiments. Other variations to the disclosed embodiments may be understood and effected by those skilled in the art in practicing the claimed invention, from a study of the drawings, the disclosure, and the appended claims.

In the claims, the word "comprising" does not exclude other elements and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

LIST OF REFERENCE SIGNS 10 optical source
20 optical source
30 spectrometer
40 spectrometer
50 channel (with or without optical fiber)
100 console
200 processing unit
300 probe
D1 first detector optical fiber
D2 second detector optical fiber
Lp1 optical path 1
Lp2 optical path 2
N nerve
S1 first source optical fiber
S2 second source optical fiber
Sp1 optical spectrum 1
Sp2 optical spectrum 2

The invention claimed is:

1. A system for detecting tissue anisotropy, the system comprising:
an optical source;
an optical detector;
a processor; and
a probe comprising a shaft with a longitudinal axis and a front end, and a plurality of optical fibers, wherein an end of each optical fiber of the plurality of optical fibers is arranged at the front end of the shaft;
wherein the plurality of optical fibers includes at least one source optical fiber configured to transmit optical radiation emitted from the optical source to irradiate a tissue and at least one detector optical fiber configured to transmit optical radiation reflected from the tissue to the optical detector;
wherein optical fibers of the plurality of optical fibers are arranged to define a plurality of optical paths between the at least one source optical fiber and the at least one detector optical fiber, wherein optical paths of the plurality of optical paths intersect at a point of intersection for optically probing the tissue at the point of intersection from a plurality of transversely-oriented directions; and
wherein the processor is configured to:
control the optical source to emit optical radiation,
receive signals generated by the optical detector as received signals, determine from the received signals a plurality of optical spectra, wherein each spectrum of the plurality of optical spectra corresponds to a corresponding optical path of the plurality of optical paths, measure optical spectra of the plurality of optical spectra, and detect anisotropy of the tissue based on differences between optical spectra of the plurality of optical spectra.

2. The system of claim 1, wherein the plurality of optical fibers comprises one detector optical fiber and two source optical fibers, wherein an optical path from a first source optical fiber to the one detector optical fiber is oriented transversely to an optical path from a second source optical fiber to the one detector optical fiber.

3. The system of claim 1, wherein the plurality of optical fibers comprises two detector optical fibers and two source optical fibers, wherein an optical path from a first source optical fiber to a first detector optical fiber is oriented transversely to an optical path from a second source optical fiber to a second detector optical fiber.

4. The system of claim 1, wherein an angle of at least 60 degrees is defined between two optical paths of the plurality of optical paths.

5. The system of claim 3, wherein an angle of at least 70 degrees is defined between two optical paths of the plurality of optical paths.

6. The system of claim 2, wherein the system comprises two optical sources.

7. The system of claim 1, wherein the system comprises an optical switch or modulator configured to distribute the optical radiation from the optical source to optical fibers of the plurality of optical fibers.

8. The system of claim 1, further comprising:
a driver configured to rotate the probe about the longitudinal axis of the probe.

9. The system of claim 1, further comprising:
polarizers configured to polarize the optical radiation emitted from the optical source.

10. The system of claim 1, wherein the probe further comprises a channel for injecting or extracting a fluid.

11. The system of claim 1, wherein the system is a diffuse reflectance spectroscopy system.

12. The system of claim 2, wherein an angle of at least 60 degrees is defined between two optical paths of the plurality of optical paths.

13. The system of claim 3, wherein an angle of at least 60 degrees is defined between two optical paths of the plurality of optical paths.

14. The system of claim 3, wherein the system comprises two optical sources.

15. The system of claim 4, wherein the system comprises two optical sources.

16. The system of claim 2, wherein the system comprises an optical switch or modulator configured to distribute the optical radiation from the optical source to optical fibers of the plurality of optical fibers.

17. The system of claim 3, wherein the system comprises an optical switch or modulator configured to distribute the optical radiation from the optical source to optical fibers of the plurality of optical fibers.

18. A non-transitory computer-readable medium having instructions stored thereon that when executed by processing circuitry cause the processing circuitry to:
control an optical source to emit optical radiation, wherein at least one source optical fiber of a plurality of optical fibers is configured to transmit optical radiation emitted from the optical source to irradiate a tissue, wherein at least one detector optical fiber of the plurality of optical fibers is configured to transmit optical radiation reflected from the tissue to an optical detector, and wherein an end of each optical fiber of the plurality optical fibers is arranged at a front end of a shaft of a probe comprising a longitudinal axis;

receive signals generated by the optical detector as received signals;

determine from the received signals a plurality of optical spectra, wherein each spectrum of the plurality of optical spectra corresponds to a corresponding optical path of a plurality of optical paths between the at least one source optical fiber and the at least one detector optical fiber, wherein optical fibers of the plurality of optical fibers are arranged to define the plurality of optical paths, wherein optical paths of the plurality of optical paths intersect at a point of intersection for optically probing the tissue at the point of intersection from a plurality of transversely-oriented directions;

measure optical spectra of the plurality of optical spectra, and detect anisotropy of the tissue based on differences between optical spectra of the plurality of optical spectra.

19. The non-transitory computer-readable medium of claim 18, further comprising instructions stored thereon that when executed by the processing circuitry cause the processing circuitry to control a rotational orientation of the probe.

20. The non-transitory computer-readable medium of claim 18, further comprising instructions stored thereon that when executed by the processing circuitry cause the processing circuitry to control a polarization direction of emitted optical radiation.

* * * * *